United States Patent [19]

Wilson et al.

[11] 4,322,361

[45] Mar. 30, 1982

[54] METHOD OF PREPARING A MANGANESE CHELATE HAVING IMPROVED PROPERTIES

[75] Inventors: David A. Wilson, Richwood; Freddie Griffin, Jr., Missouri City, both of Tex.

[73] Assignee: The Dow Chemical Company, Midland, Mich.

[21] Appl. No.: 126,792

[22] Filed: Mar. 3, 1980

[51] Int. Cl.$^3$ .............................................. C07F 13/00
[52] U.S. Cl. ........................... 260/429 J; 71/DIG. 2; 562/572
[58] Field of Search .................. 71/DIG. 2, 1, 11, 27; 260/429 J; 562/572

[56] References Cited

U.S. PATENT DOCUMENTS 4,181,672  1/1980  Popper et al. .................. 260/429 J

*Primary Examiner*—S. Leon Bashore
*Assistant Examiner*—Ferris H. Lander
*Attorney, Agent, or Firm*—A. E. Aneona

[57] ABSTRACT

Ethylenediaminetetraacetic acid and the trisodium salt of N-hydroxyethylethylenediaminetriacetic acid are mixed in water at mole ratios of 80/20 to 52/48, respectively, and a manganese compound is dissolved therein with heating. The pH is adjusted to 7 and water is added to make a solution of manganese chelate which contains 6% by wt. manganese. The resulting solution has good freeze-thaw stability.

4 Claims, No Drawings

METHOD OF PREPARING A MANGANESE CHELATE HAVING IMPROVED PROPERTIES

BACKGROUND OF THE INVENTION

Trace elements such as iron, zinc, cobalt, manganese and molybdenum are known to be necessary for the growth of healthy plants. Frequently they occur in soils, but are in a form not available to the plant. Their availability can be improved by adding certain chelating agents when these metals are present in the soil, but unavailable to plants. These metals then form chelates which are then able to be taken up by the plant. When the elements are not present in the soil, they can be added as their chelates.

Some of the most widely used of chelating agents are chelates of carboxylated and hydroxyalkylated amines, e.g., ethylenediaminetetraacetic acid, monoethanolethylenediaminetriacetic acid, diethylenetriaminepentacetic acid and the like. A description of preparing such chelates and their use in agriculture can be found in U.S. Pat. No. 3,051,563. The use of chelates is also described in U.S. Pat. No. 3,091,522.

One of the chelating agents, available commercially, for use in supplying manganese is a chelate of disodium ethylenediaminetetraacetic acid (EDTA (Na)$_2$) with manganese. It is supplied as an aqueous solution which contains 5% manganese by weight. This particular product, while giving satisfactory results with respect to supplying manganese to plants when applied to soil, nevertheless has poor storage properties in that it has a tendency to form a precipitate after undergoing numerous freeze-thaw cycles. This precipitates out some of the manganese, making the remaining solution less concentrated. In addition, the precipitate plugs up the apparatus used to dispense it. This is a disadvantage when it is stored for use under climatic conditions in which the temperature often fluctuates from above to below its freezing point.

It has now been discovered that a product which contains certain amounts of N-hydroxyethylethylenediaminetriacetic acid (HEDTA(H)$_3$) as the chelant for manganese along with the EDTA(Na)$_2$ is not affected by freeze-thaw cyclic conditions and no precipitate forms.

SUMMARY OF THE INVENTION

A composition which contains ethylenediaminetetraacetic acid (EDTA(H)$_4$) and the trisodium salt of N-hydroxyethylethylenediaminetriacetic acid (HEDTA(Na)$_3$) in the mole ratio of from 80/20 to 52/48 and manganese, present at the ratio of 0.9 to 1.0 atoms of manganese per mole of chelant, is made by mixing appropriate amounts of EDTA(H)$_4$ and HEDTA(Na)$_3$ in water and adding manganese oxide with stirring and heat. The solution of manganese chelate is adjusted to a pH of about 7 with caustic and to the desired concentration by adding water. This composition has greatly improved freeze-thaw characteristic over the aqueous composition containing Mn-EDTA(Na)$_2$.

DETAILED DESCRIPTION OF THE INVENTION

The following examples are representative of the method of preparing the manganese chelate having improved freeze-thaw characteristics:

EXAMPLE I

Ethylenediaminetetraacetic acid (87.7 g, 0.30 mole), 100 ml. of distilled water, and (166.7 g, 0.20 mole) of a 41.3% aqueous solution of the trisodium salt of N-hydroxyethylethylenediaminetriacetic acid known as Versenol® 120 were added to a reaction flask equipped with a stirrer, thermometer, and water cooled reflux condenser. Manganese oxide (34.8 g, 0.49 mole) was added with stirring and the reaction mixture heated to 95° C. for two hours and cooled. The pH was adjusted to approximately 7 with caustic solution and water added to a final manganese concentration of 6% (wt.). The solution prepared in this manner has excellent stability characteristics on undergoing freezing/thawing cycles. The product of this example contains a 60/40 mole ratio of EDTA/HEDTA and is the same as shown as Example 4 in Table I.

In preparing the manganese chelate of the present invention Mn(OH)$_2$ or MnCO$_3$ can be employed in place of MnO. Tetrasodium ethylenediaminetetraacetate [EDTA(Na)$_4$] can be substituted for ethylenediaminetetraacetic acid [EDTA(H)$_4$] if N-hydroxyethylethylenediaminetriacetic acid [HEDTA(H)$_3$] is used in place of trisodium N-hydroxyethylethylenediaminetriacetate (HEDTA(Na)$_3$). In this manner, manganese chelate solutions with high mole ratios of HEDTA(H)$_3$/EDTA(Na)$_4$ can be obtained. This technique will give manganese chelate solutions with good freeze-thaw properties but is more costly than the process based on EDTA(H)$_4$ and HEDTA(Na)$_3$.

Since the manganese chelate made from EDTA(H)$_4$ alone has poor freeze-thaw characteristics, it was unexpected that less than 50 mole percent of HEDTA (even as little as 20 mole percent) mixed with EDTA would impart good freeze-thaw characteristics to the mixture. The respective freezing points of the pure manganese HEDTA, the manganese EDTA and their mixtures are similar enough, that differences in freeze-thaw characteristics would not be anticipated. Freezing points (F.P.) of solutions of 100% EDTA-Mn, 100% HEDTA-Mn and various mixtures of the two are shown below in tabular form:

| EDTA (Mol %) | HEDTA (Mol %) | F.P. (°C.) |
| --- | --- | --- |
| — | 100 | −7.4 |
| 85 | 15 | −11.0 |
| 75 | 25 | −11.2 |
| 60 | 40 | −14.9 |
| 100 | — | −10.3* |

*6% is unstable (precipitates) even at room temperature.
A 5% solution was employed for the F.P. determination.

Thus, the freezing points are very close to one another, but the freeze/thaw characteristics are very much different, especially when subjected to repeated freeze-thaw cycles. The excellent freeze/thaw properties seem to be related to the maximum concentration of soluble manganese that can be obtained which is also dependent on the EDTA(H)$_4$/HEDTA(Na)$_3$ ratio. The influence of this ratio on solubility of the manganese chelate solution is illustrated below.

| Solubility Characteristics of Manganese Chelate Solutions* | |
|---|---|
| Mole Ratio EDTA(H)$_4$/HEDTA(Na)$_3$ | Percent Manganese in Solution |
| 100/0 | ~5.8 |
| 90/10 | ~6.0 |
| 80/20 | ~6.5 |
| 70/30 | ~7.0 |
| 60/40 | ~7.25 |
| 55/45 | ~7.25 |

*After standing for one year at 22° C.

A manganese chelate (8.5% manganese) solution prepared from HEDTA(H)$_3$, NaOH, and MnO has been stable for two years at 22° C. This represents a mole ratio of EDTA/HEDTA of 0/100.

Temperature and time factors for preparing the manganese chelate solutions are shown in tabular form below in which MnO was the manganese compound used to prepare the chelate.

| Preparation of 6% Mn Chelate Solutions | |
|---|---|
| Temperature (°C.) | Approximate Dissolution Time for MnO |
| 50 | 6-8 hours |
| 75 | 1 hour |
| 95 | ¼ hour |

The preferred temperature range for the preparation of the 6% manganese chelate solutions is 50° to 100° C.

EXAMPLE 2-12

In like manner solutions of manganese chelate were made containing various mole ratios of EDTA(H)$_4$/HEDTA(Na)$_3$.

The preferred range of EDTA(H)$_4$/HEDTA(Na)$_3$ is 80/20 to 52/48. Greater amounts of EDTA(H)$_4$ lead to stability problems with freezing/thawing. Higher amounts (greater than 48 mole percent) of HEDTA(Na)$_3$ tend to make the pH of the starting chelant mixture too high for dissolution of the MnO. The maximum amount of HEDTA(Na)$_3$ that can be used is thus governed by dissolution of the MnO. Higher ratios of HEDTA to EDTA can be obtained however by using HEDTA(H)$_3$ and EDTA(Na)$_4$ as starting materials to which to add the MnO.

Table I shows these various compositions and their freeze-thaw characteristics. Examples 9-12 are outside the scope of the invention. Each of the chelate solutions in Examples 2-9 contained 6 wt. % manganese while Examples 10-12 contained 5 wt. %. All were subjected to 10 freeze-thaw cycles. Stability upon freezing/thawing was determined by allowing samples (2 oz.) of the manganese chelate solutions to freeze at −25° C. for one week and then thaw, with no agitation, at room temperature (~22° C.). All freeze-thaw cycles were conducted in this manner.

TABLE I

| | Freeze-Thaw Characteristics Of Manganese Chelate Solutions | |
|---|---|---|
| Example | Mole Ratio EDTA(H)$_4$/ HEDTA(Na)$_3$ | Freeze-Thaw Characteristics |
| 2 | 52/48 | |
| 3 | 55/45 | |
| 4* | 60/40 | |
| 5 | 65/35 | 100% thawed in ~ 1 hour |
| 6 | 70/30 | |
| 7 | 75/25 | |
| 8 | 80/20 | |
| 9 | 85/15 | 10-15% Layer of |
| 10 | 90/10 | 10-15% solids re- |
| 11 | 95/5 | 10-15% main after |
| 12 (Comp.) | 100/0 | 10-15% 12 hours |

*The preparation of this product is shown in Example 1.

The following example is for the purpose of comparing the known art with the invention. This procedure was followed in preparing the product of Example 12 (comp.) above.

COMPARATIVE PREPARATION

Ethylenediaminetetraacetic acid (0.50 mole, 146.1 gms.), 225 ml. of distilled water and 32 gms. of 50% NaOH were added to a reaction flask equipped with a stirrer, thermometer, and water cooled reflux condenser. Manganese oxide (34.8 g, 0.49 mole) was added with stirring and the reaction mixture heated to 95° C. for two hours and cooled. The pH was adjusted to approximately 7 with caustic solution and water added to a final manganese concentration of 5%* (wt.). The solution prepared in this manner has poor stability characteristics on being subjected to freezing-thawing cycles and is shown as comparative Example 12 in Table I.

*6% solutions are not stable and will precipitate out even at temperatures above the freezing point.

The invention described in the foregoing specification is the improvement of freeze-thaw characteristics of a manganese chelate by the inclusion of at least about 20 mole percent of HEDTA(Na)$_3$ together with up to about 80 mole percent of EDTA(H)$_4$ in the preparation of the manganese chelate.

We claim:
1. A process for making a freeze-thaw stable manganese chelate solution consisting essentially of
   (1) mixing ethylenediaminetetraacetic acid and the sodium salt of N-hydroxyethylethylenediaminetriacetic acid in water in amounts so that the sodium salt of N-hydroxyethylethylenediaminetriacetic acid is from 20 to 48 mole percent of the total moles of chelate mixture,
   (2) adding to said mixture a manganese compound while heating said solution,
   (3) stirring until said manganese compound is dissolved,
   (4) cooling said solution,
   (5) adjusting the pH of said solution to about 7,
   (6) adding water to said solution to obtain the desired manganese concentration.
2. The process of claim 1 wherein said manganese compound is selected from the group consisting of MnO, Mn(OH)$_2$ and MnCO$_3$.
3. The process of claim 1 wherein the manganese concentration is adjusted to be about 6%.
4. The process of claim 1 wherein caustic is added to adjust the pH.

* * * * *